United States Patent [19]
Salas-Ceniceros

[11] Patent Number: 5,139,503
[45] Date of Patent: Aug. 18, 1992

[54] OBSTETRICAL SPATULAS

[76] Inventor: Salvador Salas-Ceniceros, Apartado Postal 11F, Durango, Mexico, 34000

[21] Appl. No.: 619,013

[22] Filed: Nov. 28, 1990

[51] Int. Cl.⁵ .............................................. G01N 3/48
[52] U.S. Cl. .................................. 606/122; 606/208; 606/121
[58] Field of Search ................ 606/121, 122, 124, 208

[56] References Cited

U.S. PATENT DOCUMENTS

| | | | |
|---|---|---|---|
| 399,749 | 3/1889 | Galiano | 606/122 |
| 820,845 | 5/1906 | Barton | 606/122 |
| 930,886 | 8/1909 | Robertson | 606/122 |
| 1,048,728 | 12/1912 | Norden | 606/122 |
| 1,619,299 | 3/1927 | Hylarides | 606/122 |
| 2,639,712 | 5/1953 | Miseo | 606/122 |
| 3,088,465 | 5/1963 | Smith | 606/122 |
| 3,605,748 | 9/1971 | Salinas-Benavides | 606/124 |
| 3,785,381 | 1/1974 | Lower et al. | 606/122 |

FOREIGN PATENT DOCUMENTS

| | | | |
|---|---|---|---|
| 2406431 | 5/1979 | France | 606/122 |

*Primary Examiner*—Peter A. Aschenbrenner
*Attorney, Agent, or Firm*—Fleit, Jacobson, Cohn, Price, Holman & Stern

[57] ABSTRACT

A pair of obstetrical spatulas especially useful during the second stage or expulsion stage of labor during childbirth to assist in helping the fetal head to exit from the pelvic outlet by closely simulating the normal movements of the fetal head in the birth canal. Each spatula includes a blade provided with cephalic curve configuration to conform with and engage the fetal head with the blades including a shank or pedicule which form an angle of approximately 35° with the longitudinal axis of the blades to provide a perineal curve. The pedicules are connected to a semicircular segment by a hinge at each end of the semicircular segment to enable articulate movement of the pedicules and blades in directions toward and away from each other and in longitudinal or axial directions. One of the hinge connections between the pedicule and semicircular segment is separable to enable more effective and accurate positioning of the blades in relation to the fetal head and pelvic outlet by individually positioning the blades after which the hinge is connected. A traction bar and handle with a force indicator is connected to the semicircular segment to control and indicate the traction force exerted on the spatulas.

11 Claims, 1 Drawing Sheet

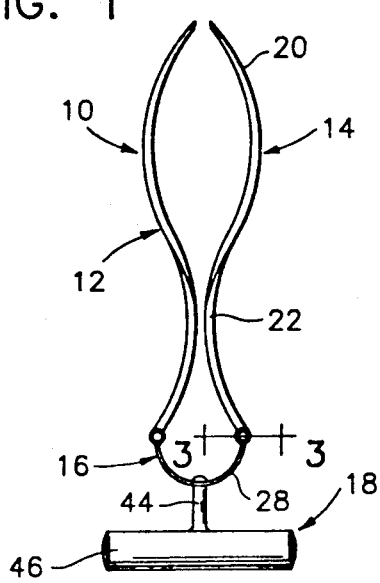
FIG. 1
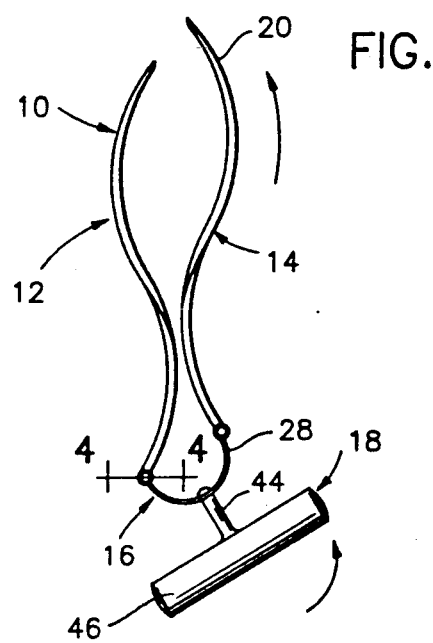
FIG. 2
FIG. 3
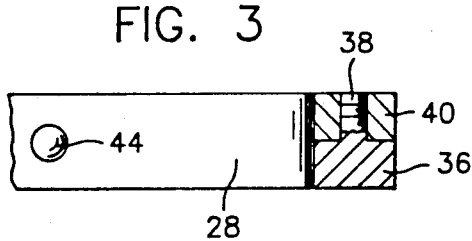
FIG. 4
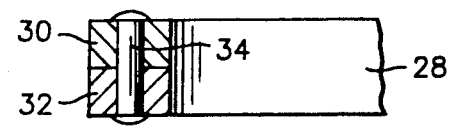
FIG. 5
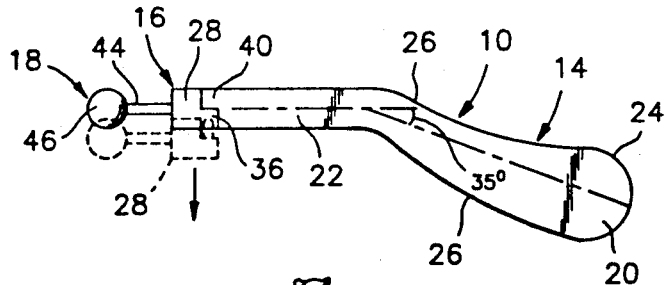
FIG. 6
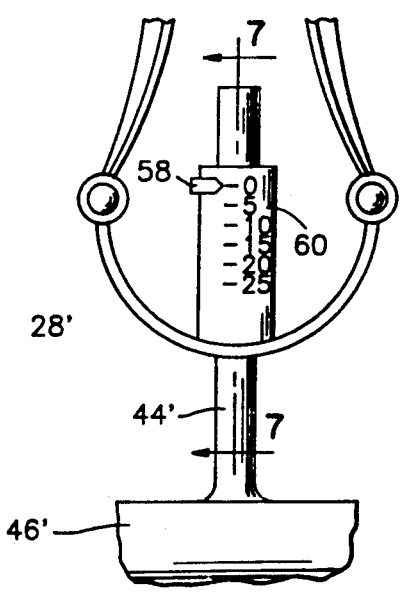
FIG. 7
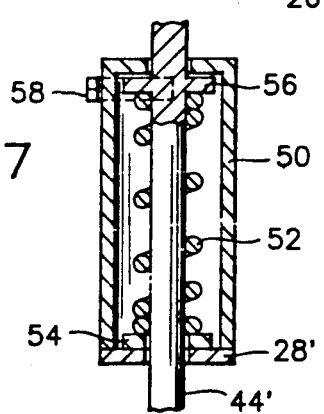

OBSTETRICAL SPATULAS

BACKGROUND OF THE INVENTION

1. FIELD OF THE INVENTION

The present invention generally relates to a pair of obstetrical spatulas especially useful during the second stage or expulsion stage of labor during childbirth. The spatulas assist in helping the fetal head to exit from the pelvic outlet by closely simulating the normal movements of the fetal head in the birth canal. The spatulas include blades provided with cephalic curve configuration to conform with and engage the fetal head with the blades including a shank or pedicule which form an angle of approximately 35° with the longitudinal axis of the blades to provide a perineal curve. The pedicules are connected to a semicircular segment by a hinge at each end of the semicircular segment to enable articulate movement of the pedicules and blades in directions toward and away from each other and in longitudinal or axial directions. One of the hinge connections between the pedicule and semicircular segment is a separable connection to enable more effective and accurate positioning of the blades in relation to the fetal head and pelvic outlet while the blades and pedicules can be individually positioned after which the hinge is connected. A traction bar and handle with a force indicator is connected to the semicircular segment to control and indicate the traction force exerted on the spatulas. The spatulas are constructed of stainless steel and are compressed rather than being forged to enable the blades to be quite thin for easy insertion and application to the fetal head while maintaining appropriate strength for this purpose.

2. DESCRIPTION OF THE PRIOR ART

Obstetrical forceps have been developed and are in use to assist movement of a fetus through the birth canal. Such devices have the disadvantage of introduction of cephalic compression which may become excessive and thus injurious to the fetus and also can introduce excessive traction forces to the fetus. The following U.S. patents are relevant to obstetrical forceps.

U.S. Pat. No. 820,845
U.S. Pat. No. 1,009,475
U.S. Pat. No. 2,639,712
U.S. Pat. No. 3,088,465
U.S. Pat. No. 3,605,748
U.S. Pat. No. 3,665,925

The above listed patents do not disclose the specific structure of the pair of spatulas of this invention and do not disclose an articulable pair of spatulas with an axial traction system for assistance in the birth of a fetus during the second stage or expulsion period of labor.

SUMMARY OF THE INVENTION

An object of the present invention is to provide a pair of obstetrical spatulas especially adapted for use during the second stage of labor to move the fetal head in a manner to facilitate exit from the pelvic outlet in the event physical characteristics are retarding or preventing exit from the pelvic outlet or when it is desired to shorten or terminate the second stage of labor as promptly as possible in order to avoid or prevent distress to the fetus by simulating the normal movements of the fetal head in the birth canal in order to reduce or eliminate application of excessive forces on the fetus which can result in stress or injury during birth. The spatulas each include a blade provided with optimum cephalic curvature to properly fit and engage the fetal head with the blade including a shank or pedicule extending from one end thereof at an angle of approximately 35° to provide a perineal curve.

Another object of the invention is to provide a pair of obstetrical spatulas in accordance with the preceding object in which the pedicules are interconnected at their end distal from the blades by a semicircular connecting member hingedly connected to the spatulas to enable articulate movement of the spatulas toward and away from each other and axially in relation to each other thereby enabling optimum movement capabilities of the fetal head to facilitate exit from the pelvic outlet and movement throughout the birth canal.

A further object of the invention is to provide a pair of obstetrical spatulas which are articulable in which one of the spatulas is separable from the connecting member at the hinge connection between the spatula and connecting member to enable the spatulas to be individually and accurately positioned in relation to the birth canal, pelvic outlet and fetal head when the spatulas are separated from each other thereby enabling more accurate positioning of the spatulas without stress to the fetus with the separate spatula being hingedly connected to the connecting member after the spatulas have been connected.

Still another object of the invention is to provide a pair of obstetrical spatulas as set forth in the preceding objects in which the connecting member is semicircular in configuration and provided with a traction bar and handle attached centrally thereto with the traction bar including a force indicator to indicate the traction force exerted on the pair of spatulas thereby enabling accurate control and indication of the forces exerted on the fetus to reduce or eliminate the possibility of stress or injury by excessive traction force.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a plan view of the pair of obstetrical spatulas of the present invention illustrated in their unarticulated position.

FIG. 2 is a plan view similar to FIG. 1 but illustrating the pair of spatulas in an articulated position.

FIG. 3 is a detail sectional view taken along section line 3—3 on FIG. 1 illustrating the construction of the separable hinge between one end of a connecting member and a spatula.

FIG. 4 is a transverse sectional view illustrating the permanent hinge connection between the other end of the connecting member and the other spatula.

FIG. 5 is a side elevational view of the spatulas illustrating the perineal curve of the blades and pedicules.

FIG. 6 is a fragmental plan view illustrating a force indicator incorporated between the traction bar and handle and the connecting member between the pair of spatulas.

FIG. 7 is a longitudinal, sectional view taken along section line 7—7 on FIG. 6 illustrating specific structural details of the force indicator.

DESCRIPTION OF THE PREFERRED EMBODIMENTS

Referring now specifically to the drawings, the pair of obstetric spatulas of the present invention is generally designated by reference numeral 10 with the individual spatulas being designated by reference numerals 12 and 14 respectively with the spatulas being interconnected at one of their ends by a connecting member generally designated by numeral 16 having a traction system generally designated by the numeral 18 connected centrally to the connecting member 16. FIG. 1 illustrated the spatulas 12 and 14 when in their aligned, unarticulated position while FIG. 2 illustrates the spatulas moved axially in relation to each other to their articulated position to facilitate correction of the position of the fetal head when in asinclitic positions.

As illustrated in FIG. 5, each of the spatulas are identical and the spatula 14 as well as the spatula 12 includes a blade 20 having a shank or pedicule 22 forming an extension of one end of the blade 20. The blade 20 included a curved outer end edge 24 and curved and generally converging side edges 26 extending therefrom for merging with the top and bottom edges of the pedicule 22. The longitudinal axis of the blade 14 is oriented at an angle of approximately 35° to the longitudinal axis of the pedicule as illustrated in FIG. 5 to define the perineal curve. The blade 20 includes a convex outer surface and a concave inner surface to define a cephalic curve to engage and conform with the surface areas of the fetal head to enable forces to be exerted on the fetal head without excessive compressive forces being exerted on the fetal head.

The connecting member 16 includes a semicircular rigid member 28 having the same width as the pedicule 22. The spatula 12 is connected to the connecting member 28 by the use of a hinge lug 30 on the pedicule 22 and a hinge lug 32 on the member 28 with a hinge pin 34 permanently and hingedly connecting these two components together. The other spatula 14 is detachably and hingedly connected to the other end of the semicircular member 28 by a hinge lug 36 on the semicircular member 28 provided with an upstanding hinge pin 38 located thereon. The pedicule 22 of the spatula 14 includes a hinge lug 40 thereof which fits down over the upstanding hinge pin 38. The hinge pin 38 is not enlarged at the outer end thereof thus enabling the pedicule 22 on the spatula 14 to be lifted off the pin 38 or positioned over the pin 38 thereby providing a separable hinge connection. This feature enables the blades 20 of the separated spatulas to be inserted between the fetal head and the pelvic cavity and outlet or the birth canal individually and separately with the outer ends of the spatulas being connected to each other after positioning by engaging the hinge lug 40 on the spatula 14 with the pin 38. The articulate connection between the spatulas 12 and 14 and the connecting member 28 enables articulation of the spatulas between the unarticulated position in FIG. 1 and the articulated position in FIG. 2 or the opposite articulated position.

The traction assembly 18 includes a traction bar 44 rigidly affixed to the center of the semicircular member 38 and a transverse handle 46 rigid with the traction bar. The handle 46 enables articulation of the spatulas to enable sufficient lateral displacement to correct asinclitic positions of the fetal head. The person using the spatulas can properly move and position the fetal head by the use of a low traction force exerted by a single hand when fetal cephalic compression is not required thereby protecting the fetal head from excessive compressive forces and excessive traction forces.

FIGS. 5 and 6 illustrate an optional embodiment of the invention in which the fetal bar 44' having the handle 46' thereon is not rigidly connected to the center of semicircular member 28'. Rather, the traction bar 44' extends through the center of the semicircular member 28' and through a tubular sleeve 50 rigid with the member 28. The sleeve includes a coil spring 52 encircling the traction bar 44' with one end engaging a washer or the like 54 positioned against the surface of the member 28 and the other end engaging a flange 56 on the traction bar 44' as illustrated in FIG. 7. The traction bar 44' includes a pointer or indicator 58 attached thereto and extending outwardly through a suitable slot in the sleeve 50 for association with numerical indicia and a graduated scale 60 as illustrated in FIG. 6 thus indicating the traction force exerted on the pair of spatulas by the handle 46' thereby further reducing the possibility of stress or injury to the fetus.

The spatulas are interconnected by the connecting member 28 in order for the spatulas to diverge in relation to each other when engaged with the fetal head. The spatulas are constructed from stainless steel which are formed by a compression technique rather than forging which enables the blades to be quite thin thereby facilitating easy insertion of the blades into position in relation to the fetal head. This blade structure together with the perineal curve provides an effective engagement with the fetal head with the articulation enabling movement of the spatulas and thus the fetal head in a universal manner since the handle and traction bar can exert traction forces and enable single handed operation when traction forces are applied and also facilitates angular movement about the longitudinal axis of the traction bar.

While dimensional characteristics may vary, it has been found that the pair of spatulas function effectively when the overall length of the spatulas is 13⅛" (33.5 cm), provided with a thickness of stainless steel of 1.5 mm and weighing 14.5 oz (425 g) thus providing an instrument that is lighter in weight than existing obstetrical forceps with the lightness and thinness of the blades resulting from compression of the stainless steel rather than forging. The blades are 3.74" (9.5 cm) in length, 0.87" (2.2 cm) in width with the blades being at a 35° angle in relation to the pedicule to form the perineal curve in order to avoid damage to the maternal perineum. The hinges provide a wide range of mobility with one of the hinges being seperable. The semicircular member 28 has a diameter of 1.77" (4.5 cm) and the traction bar is 1.1" (2.8 cm) in length and 2.4" (6 mm) in width. The traction handle is 4.33" (11 cm) in length and 0.98" (2.5 cm) in width to enable one hand operation of the spatulas. The hinges provide displacement of the spatulas in an angular direction as well as an axial direction to correct asinclitic positions of the fetal head. The spatulas replace traditional forceps that sometimes produce excessive compressive or traction forces on the fetus. Existing forceps generally in the form of pincers sometimes place an excessive force of traction since they are operated with both hands. With this invention, only one hand is necessary and no excessive compression force occurs. Thus, the traction system which is operated with one hand provides significant advantages in operation of the spatulas.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. An apparatus for assisting in the delivery of a baby during the second stage or expulsion stage of labor comprising a pair of spatulas, a connecting member hingedly connected to and extending between one end of the spatulas to enable the spatulas to be positioned in generally coextensive diverging relation from the connecting member when in use, a traction assembly attached centrally to the connecting member and including handle means connected to the connecting member to enable the connecting member to be pivoted to an angular position to orient one spatula generally longitudinally adjusted in relation to the other spatula to facilitate exit of the fetal head from the pelvic outlet of a mother and to correct asinclitic positions of the fetal head during birth.

2. The obstetrical spatulas as defined in claim 1 wherein each of said spatulas includes an elongated shank extending from the blade to the connection with the connecting member, said blade being downwardly angled at approximately 35° to the longitudinal axis of the shank to define a perineal curve.

3. The obstetrical spatulas as defined in claim 1 wherein the connection between the connecting member and one of said spatulas is a detachable hinged connection to enable the spatulas to be inserted into operative association with a fetal head while in separated condition with the separated spatulas being connected to the connecting member after positioning of the blades in relation to the fetal head.

4. The obstetrical spatulas as defined in claim 1 wherein said traction bar assembly includes a substantially T-shaped structure including a handle connected to the connecting member at the central portion thereof to enable traction force to be exerted on the spatulas by one hand of a person using the spatulas.

5. The apparatus as defined in claim 1 wherein each of said spatulas includes a blade having a curved configuration conforming with an optimum cephalic curve of the fetal head with the blades including a downwardly curved portion defining a perineal curve.

6. The apparatus as defined in claim 5 wherein said connecting member is semicircular in configuration, said handle means including a T-shaped handle, said handle having a shank connected with the central portion of the connecting member.

7. The apparatus as defined in claim 6 wherein said handle is rigid and the shank is rigidly connected to said connecting member.

8. The apparatus as defined in claim 6 wherein said shank is connected to said connecting member through a spring biased, force indicating means to indicate the traction force exerted on the spatulas.

9. Obstetrical spatulas comprising a pair of spatulas in the form of elongated members having a curved blade at one end, a connecting member extending between and hingedly connected to the other end of the spatulas, a traction bar assembly connected to the connecting member intermediate the hinge connections between the connecting member and spatulas, each spatula including an elongated shank extending from the blade to the connecting member, said blade on each spatula being curved downwardly from the shank to define a perineal curve with the entire blade being disposed below a horizontal plane along the upper edge of the shank.

10. The obstetrical spatula as defined in claim 9 wherein said traction bar includes a rigid handle having a longitudinal axis in alignment with the longitudinal axis of the connecting member to enable traction force to be exerted on the spatulas by using only one hand.

11. The obstetrical spatulas as defined in claim 10 wherein the spatulas are hingedly connected to the connecting member by hinge connections having a pivot axis perpendicular to the longitudinal axis of the connecting member to enable the spatulas to be moved longitudinally in relation to each other by using one hand to move the handle and connecting member to angular positions about a transverse axis with the blades being supported by the vaginal walls and engaged with the fetal head.

* * * * *